(12) United States Patent
Eick et al.

(10) Patent No.: US 9,217,799 B2
(45) Date of Patent: Dec. 22, 2015

(54) DISTINCTIVE LAND SEISMIC SWEEP

(71) Applicant: CONOCOPHILLIPS COMPANY, Houston, TX (US)

(72) Inventors: Peter M. Eick, Houston, TX (US); Joel D. Brewer, Houston, TX (US); Shan Shan, Houston, TX (US)

(73) Assignee: ConocoPhillips Company, Houston, TX (US)

( * ) Notice: Subject to any disclaimer, the term of this patent is extended or adjusted under 35 U.S.C. 154(b) by 423 days.

(21) Appl. No.: 13/874,168

(22) Filed: Apr. 30, 2013

(65) Prior Publication Data

US 2013/0286780 A1 Oct. 31, 2013

Related U.S. Application Data

(60) Provisional application No. 61/640,432, filed on Apr. 30, 2012.

(51) Int. Cl.
| | |
|---|---|
| *G01V 1/155* | (2006.01) |
| *G01V 1/09* | (2006.01) |
| *G01V 1/00* | (2006.01) |
| *G01V 1/24* | (2006.01) |
| *G01V 1/147* | (2006.01) |
| *A01N 47/40* | (2006.01) |
| *A01N 57/20* | (2006.01) |
| *G01V 1/145* | (2006.01) |

(52) U.S. Cl.
CPC ............... *G01V 1/155* (2013.01); *A01N 47/40* (2013.01); *A01N 57/20* (2013.01); *G01V 1/005* (2013.01); *G01V 1/09* (2013.01); *G01V 1/147* (2013.01); *G01V 1/24* (2013.01); *G01V 1/145* (2013.01)

(58) Field of Classification Search
CPC ....... G01V 1/09; G01V 1/143; G01V 1/1047; G01V 1/147; G01V 1/145; G01V 1/155
USPC ......................................... 181/111, 114, 121
See application file for complete search history.

(56) References Cited

U.S. PATENT DOCUMENTS

| | | | | |
|---|---|---|---|---|
| 2,675,882 | A * | 4/1954 | Bazzoni et al. ............... | 181/111 |
| 3,777,843 | A * | 12/1973 | Fair et al. ...................... | 181/114 |
| 4,114,722 | A * | 9/1978 | Weber et al. .................. | 181/114 |

(Continued)

*Primary Examiner* — Ari M Diacou
(74) *Attorney, Agent, or Firm* — ConocoPhillips Company

(57) ABSTRACT

The invention is an electric sweep type seismic vibrator source of the type used in seismic prospecting for hydrocarbons. The source uses an engine and generator combination to create electric power for all systems on the source such as driving a frame of linear electric motors that direct a rod or piston to contact the ground in a recurring fashion along with driving the source from location to location through a survey area. Preferably a foot is arranged on the bottom end of the rod or piston for contact with the ground and by engaging the grid of motors to push down against the ground in a rapid progression, acoustic energy is created and delivered into the ground for geophones to sense and record. However, the rapid progression of pulses or sweep of seismic energy is delivered in a distinctive fashion as compared to a conventional upsweep or downsweep and the distinctiveness is also achieved by creating a designed cadence or timing such that each pulse in a series of pulses is not delivered in a regular timing. Several similar seismic sources may be employed where each is provided with its own distinctive series of pulses such that each may be identified within the data record and source separation from a number of seismic sources may be accomplished.

4 Claims, 2 Drawing Sheets

(56) References Cited

U.S. PATENT DOCUMENTS

| | | | |
|---|---|---|---|
| 4,133,409 A * | 1/1979 | Mifsud et al. | 181/114 |
| 4,372,420 A * | 2/1983 | White | 181/120 |
| 4,458,777 A * | 7/1984 | Weber et al. | 181/121 |
| 4,651,044 A * | 3/1987 | Kompanek | 310/323.17 |
| 4,853,906 A * | 8/1989 | Cole | 367/189 |
| 5,614,670 A * | 3/1997 | Nazarian et al. | 73/146 |
| 7,330,401 B2 | 2/2008 | Jeffryes et al. | |
| 7,657,350 B2 * | 2/2010 | Moran | 701/22 |
| 7,668,262 B2 | 2/2010 | Woo et al. | |
| 7,841,444 B2 * | 11/2010 | Cannell et al. | 181/121 |
| 8,256,565 B2 * | 9/2012 | Pabon et al. | 181/104 |
| 2003/0168277 A1 * | 9/2003 | Hopperstad et al. | 181/111 |
| 2006/0250891 A1 | 11/2006 | Krohn | |
| 2010/0232260 A1 * | 9/2010 | Zowarka et al. | 367/189 |
| 2011/0209940 A1 * | 9/2011 | Daraio | 181/139 |
| 2012/0037444 A1 * | 2/2012 | Eick et al. | 181/114 |
| 2013/0155817 A1 * | 6/2013 | Kim | 367/189 |

\* cited by examiner

DISTINCTIVE LAND SEISMIC SWEEP

CROSS-REFERENCE TO RELATED APPLICATIONS

This application is a non-provisional application which claims benefit under 35 USC §119(e) to U.S. Provisional Application Ser. No. 61/640,432 filed Apr. 30, 2012, entitled "DISTINCTIVE LAND SEISMIC SWEEP," which is incorporated herein in its entirety.

STATEMENT REGARDING FEDERALLY SPONSORED RESEARCH

None.

FIELD OF THE INVENTION

This invention relates to vibratory seismic sources and particularly to seismic sources that are held to the ground to deliver vibratory impulses into the earth for seismic prospecting of hydrocarbons and other subsurface resources.

BACKGROUND OF THE INVENTION

In the process of acquiring seismic data, seismic energy is delivered into the earth. Over the years, the preferred attributes of the seismic energy delivered into the earth have been honed to include a broad spectrum of wavelengths and sufficient power across the spectrum to be recorded at the surface. In general, a suitable land source must be able to deliver seismic energy waves in a spectrum of wavelengths from about 8 Hz up to 60-80 Hz. The source must have sufficient power across the spectrum so that the seismic waves have measurable amplitude at the surface after transiting deep into the earth, reflecting from or refracting through layers in the earth and transiting back to the surface. A last major characteristic of a desirable seismic source is that the energy from the source is distinguishable in the data record from seismic energy from other sources whether from background sources or other seismic prospecting.

Explosive charges have long been used as seismic sources although the intense release of energy is typically not permitted except in remote locations. Explosive sources, however, provide a wide array of wavelengths with considerable power across the wavelengths.

Hydraulic reciprocating seismic vibrators or vibes have been in use for many years using a baseplate connected to hydraulic rams that cause a reaction mass to reciprocate up and down to shake the ground through the baseplate. The hydraulic rams are operated to move the reaction mass through a sweep of the desired frequencies. However, the hydraulic systems are limited in their ability to provide sufficient power at high frequencies due to limitations of hydraulic flow in and out of the hydraulic cylinders. At very high hydraulic velocities, the hydraulic fluid is subject to cavitation effects when reversing directions that limits the amplitude of the movement of the reaction mass and thus the energy input in to the earth. At low frequencies, it is difficult for the hydraulic vibe to have enough travel to generate a low frequency wave into the ground. For example, consider how one would generate a one Hz wave with a hydraulic vibe. A very long throw of the reaction mass is needed to generate that wavelet because the mass has to be moving down and up the full one second.

BRIEF SUMMARY OF THE DISCLOSURE

The invention more particularly relates to a process for delivering a distinctive seismic sweep for a seismic prospecting operation wherein an electrically powered seismic source is provided that has a plurality of linear electric motors where a ground contact element of the linear electric motor is provided in contact with the ground. The ground contact elements of linear electric motors are driven to deliver multiple impulses against the ground in a manner to create a distinctive composite sweep to convey seismic energy into the earth.

"Generally vertical" or "generally vertically" should be interpreted as meaning "with an axis of movement sufficiently nearly vertical with respect to the ground so as effectively to impart energy to the ground." Normally, the axis of movement would be less than 20 degrees to vertical, or in another embodiment less than 10 degrees to vertical.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

Figure 1:
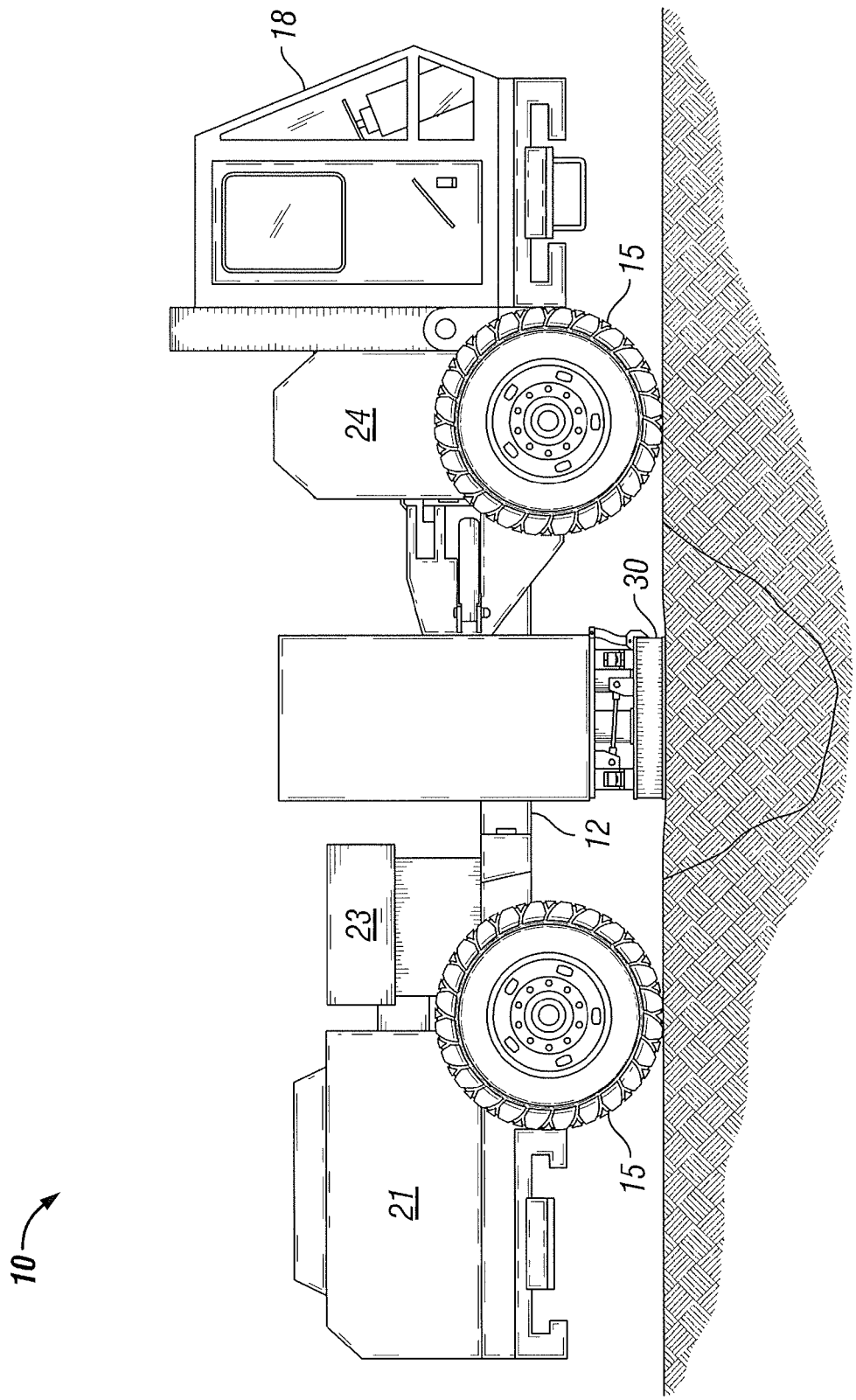
FIG. 1 is an elevation view of a discrete electric seismic source unit.

As shown in FIG. 1, an alternative vibrator actuator source 10 is shown comprising a chassis 12, four wheels 15 and a driver's cab 18. The alternative vibrator actuator source 10 uses a diesel engine 21 to turn an electric generator 23 and uses electric power to power the source 10 both for delivering acoustic energy into the ground and for moving along the ground from location to location. The source 10 utilizes electricity for all of its power needs. A large battery 24 is included to store energy for high situations of high electrical demand or when there are problems with the generator 23, but the battery 24 provides the power to return to a location for repair.

Figure 2:
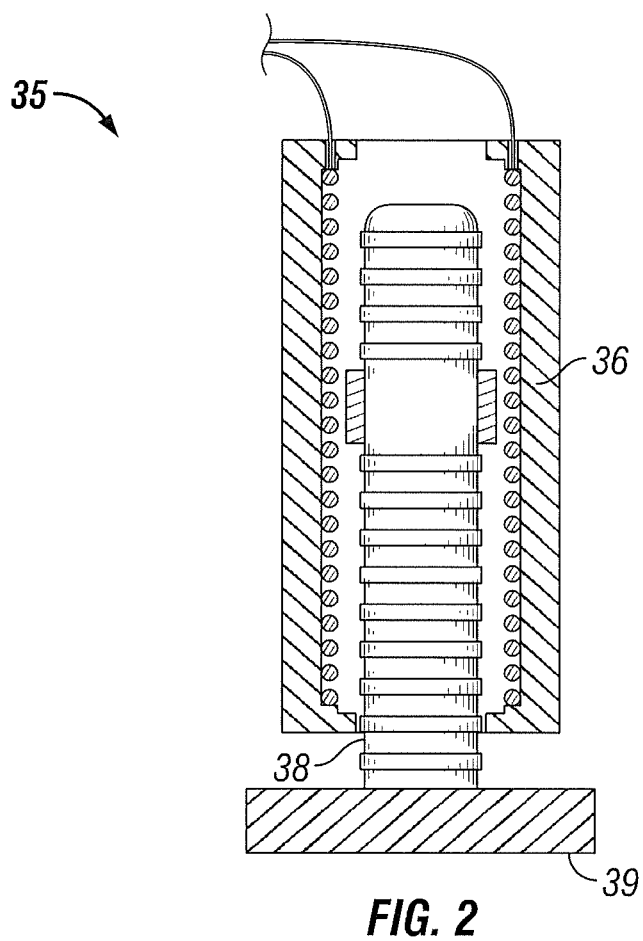
FIG. 2 is an enlarged fragmentary view of an electromechanical linear motor assembly for delivering seismic energy into the ground.
Figure 3:
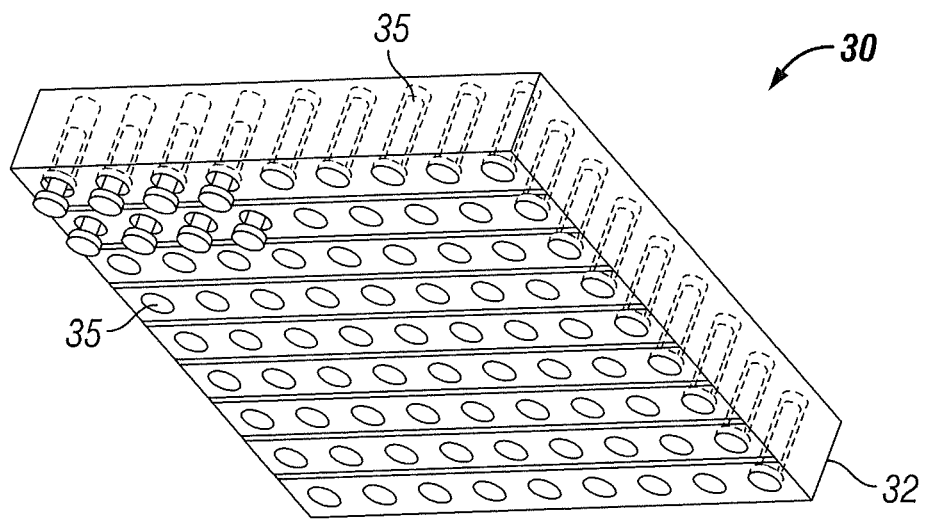
FIG. 3 is an enlarged perspective fragmentary view of a grid of electro mechanical linear motor assemblies for cooperatively delivering seismic energy into the ground.

Referring now to FIGS. 2 and 3, the acoustic energy delivery system 30 is carried under the chassis 12 and comprises a frame 32 that carries a number of linear motors 35. Each linear electric motor 35 includes a tubular body 36 and a rod or actuation bar 38 positioned within the tubular body 36 that extends telescopically from the lower end of the tubular body 36. A replaceable foot 39 is attached to the bottom end of the rod 38 for contacting the ground. The frame 32 includes mounts for a grid of linear motors 35. In the preferred embodiment approximately 112 linear motors 35 are arranged in a grid of perhaps 8 by 14.

In operation, the frame 32 is lowered into proximity to the ground G and the linear motors 35 are operated to lower the replaceable feet 39 into contact with the ground G. Once all of the replaceable feet 39 are in contact with the ground G, the linear motors 35 are activated to thrust the rods 38 toward the ground G and deflect the ground G and thereby deliver an impulse into the earth. The linear motors 35 are quickly operated to recoil the rods 38 without disengaging contact with the ground G by the replaceable feet 39. By successive thrusts and recoils, a pattern of acoustic energy is effectively delivered into the earth while the feet remain in contact with the ground G. It should be noted that the undulations and irregularities of the ground G may be accommodated avoiding decoupling across the dimension of the frame 32. This method may be arranged to automatically compensate for surface topographic variations along with soft and hard spots on the ground surface like rocks or logs. While it is recognized that ground typically does not deflect much, it does not take much deflection with a 60,000 pound vibrator holding the replaceable feet 39 to the ground G to deliver very useful acoustic energy. In this procedure, all of the linear motors 35 would be operated at the same time in the same direction using electrical power created by the electric generator 23 and supplemental battery 24 power if needed. The impulses would be repeated in a sequence where the impulse would occur with progressively increasing or decreasing rapidity such that a progression of frequencies of impulse forces would effectively deliver acoustic energy into the earth. The acoustic energy being characterizeable as a progressive pattern of frequencies covering a spectrum from about 1 Hz up to at least 80 Hz and preferably up to 120 Hz similar to a sweep.

The selection of the specific linear motors is an engineering issue at production time because they can be sourced to have a large thrust force but with short strokes as compared to those that have longer strokes with less thrust, but higher speeds. As one embodiment of the invention, the frame 32 has approximately 112 linear motors 35 that are arranged in a grid of perhaps 8 by 14. Each linear motor is capable of outputting a peak acceleration force of approximately 2400 Newtons (N) or approximately 540 pounds-force while using 34 amps RMS (Arms) at 240 volts AC. The 112 linear motors would then be capable of outputting 268,800 N or 60,480 pounds-force using approximately 914 kilowatts of power. An array of 112 of these motors could operate in the space provided and would require approximately a 1225 Hp diesel electric motor and generator providing the prime mover power source assuming reasonable losses in energy conversion.

One advantage of using a plurality of linear electric motors as proposed by the present invention is that other operational modes become available and useful. According to the present invention, very creative sweeps may be delivered such that high frequencies, low frequencies and intermediate frequencies may be delivered in an irregular pattern that forms a distinguishable pattern in the data record that may be easily attributable to the source that delivered that energy into the ground. Ideally, a unique and highly distinctive sweep or series of pulses or actuations of the linear motors 35 may be delivered. At the moment, the only limitations are that the cumulative time at any one frequency should be reasonably consistent across the spectrum and the sweep should fully populate the entire spectrum. Even this restriction can be mitigated if one is willing to deal with a variable background noise level because actuation of the source at different frequencies for different lengths of time sets up a variable signal to noise ratio. The unique sweeps may be creatively designed such that multiple seismic vibes may deliver seismic energy at the same time where each vibe has its own distinctive sweep and the resulting seismic data may be inverted to identify which source at which location provided the source for each signal.

This new capability allows many vibes to be delivering seismic energy into the ground in nearby locations without interfering with one another or creating the need for time sharing. There are techniques for operating a gang or fleet of vibes concurrently, but they require starting the sweeps for all the vibes together so that they may be distinguished by phase offset. Phase offset works as in HFVS or ZenSeis®, but using a highly distinctive sweeps would likely provide higher clarity in distinguishing the energy of each vibe and stabilize the inversion and separation matrix more fully.

For clarity, the distinctive sweeps may be constructed much like a song that uses the frequency of "notes" along with a cadence between the notes. In a seismic sweep, the frequency range or spectrum is much broader, starting at about 6 Hz, but possibly lower and extending up to at least 60 Hz and typically up to 80 to 100 Hz. Given the capability of the linear motors, this could be extended downward to near 1 Hz on the low end and significantly higher on the high end, for example at least 150 Hz.

While a song may not utilize all the range of musical notes, a seismic sweep should include portions covering the entire range and should be balanced across the range. The timing or cadence of the sweep may also include gaps to add to uniqueness. Ultimately, the potential permutations of sweeps can make for a great many sweeps that all have very distinctive attributes that are easily identifiable in the data record. For example, the series of impulses provide seismic energy across a frequency spectrum wherein the series of impulses are distinctive or distinguishable from other sweeps of seismic energy due to an irregular, but distinctive order of progression through the frequency spectrum. The other seismic energy may be from other vibes within a survey or in a completely separate survey on nearby land. The impulses may also be distinctive or distinguishable from other sweeps due to a distinctive cadence or irregular time delays between the impulses.

As an analogy, this distinctive sweep approach to the sourcing of energy could be equated to what occurs when you are in a crowded party and everyone is talking at once. While there is a great deal of background noise occurring, if you are concentrating on a particular person you can discern their voice from the noise of the background. The distinctive sweep would achieve the same result.

Another way to think of the invention is to think of the comparison between a distinctive sweep made up of say "Country" music vs. "Opera" music. If both were bandlimited to the sweep frequencies desired, and then power balanced to maintain consistent signal to noise ratios in all bands, then they would be quite unique and easily identifiable. This can be easily shown with any of the digital signal processing software packages and common MP3 files. Casual listening to the differences between the "songs" after a bit of digital filtering shows how distinct they can be made. The key inventive insight is that the linear motor offers the seismic acquisition designer access to a stereo like loudspeaker that can be manipulated to produce a distinctive sweep in very non-traditional methods which a hydraulic vibrator is incapable of producing.

In closing, it should be noted that the discussion of any reference is not an admission that it is prior art to the present invention, especially any reference that may have a publication date after the priority date of this application. At the same time, each and every claim below is hereby incorporated into this detailed description or specification as a additional embodiments of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A process for delivering a distinctive seismic sweep for a seismic prospecting operation, the process comprising:
   a) providing an electrically powered seismic source having about 100 to 5,000 linear electric motors carried by a frame, wherein a ground contact element of the linear electric motor is provided in contact with the ground; and
   b) driving the ground contact elements of linear electric motors to deliver multiple impulses against the ground in a manner to create a distinctive series of impulses to convey seismic energy into the earth.

2. The process for delivering acoustic energy into the earth according to claim 1, further including the step of receiving and recording the seismic energy returning to the surface of the earth.

3. The process for delivering acoustic energy into the earth according to claim 1, wherein the series of impulses comprises seismic energy across a frequency spectrum and wherein the series of impulses are distinctive or distinguishable from other sweeps of seismic energy due to an irregular, but distinctive order of progression through the frequency spectrum.

4. The process for delivering acoustic energy into the earth according to claim 1, wherein the impulses are distinctive or distinguishable from other sweeps due to a distinctive cadence or irregular time delays between the impulses.

* * * * *